(12) United States Patent
Fujii

(10) Patent No.: US 7,689,026 B2
(45) Date of Patent: Mar. 30, 2010

(54) METHOD FOR TESTING IMAGE PROCESSING CIRCUIT, PARTICLE IMAGE ANALYZER, AND STORAGE MEDIUM

(75) Inventor: Kozo Fujii, Akashi (JP)

(73) Assignee: Sysmex Corporation, Kobe (JP)

( * ) Notice: Subject to any disclaimer, the term of this patent is extended or adjusted under 35 U.S.C. 154(b) by 1181 days.

(21) Appl. No.: 11/218,166

(22) Filed: Aug. 31, 2005

(65) Prior Publication Data

US 2006/0047460 A1 Mar. 2, 2006

(30) Foreign Application Priority Data

Aug. 31, 2004 (JP) ............................. 2004-253283

(51) Int. Cl.
*G06K 9/00* (2006.01)
(52) U.S. Cl. ...................................... 382/141
(58) Field of Classification Search .................. 382/141
See application file for complete search history.

(56) References Cited

U.S. PATENT DOCUMENTS

| 5,721,433 | A | 2/1998 | Kosaka | |
|---|---|---|---|---|
| 7,352,900 | B2* | 4/2008 | Yamaguchi et al. | 382/192 |
| 2003/0031356 | A1* | 2/2003 | Sasa | 382/145 |
| 2004/0057634 | A1* | 3/2004 | Mutoh | 382/298 |

* cited by examiner

*Primary Examiner*—Bhavesh M Mehta
*Assistant Examiner*—Hadi Akhavannik
(74) *Attorney, Agent, or Firm*—Brinks Hofer Gilson & Lione

(57) ABSTRACT

A particle image analyzer provided with an image processor for executing predetermined image processes on a particle image containing an image of a particle, a reading means for reading test result data from a flash memory card on which are previously recorded test result data equivalent to the processing result of the image processor during normal operation, and a testing means for determining whether or not the image processor is operating normally by comparing the processing result obtained when the test image is used in the image processor, and test result data read from the flash memory card by the reading means.

22 Claims, 16 Drawing Sheets

Prime code : 11110001(bin)=F1(hex)

METHOD FOR TESTING IMAGE PROCESSING CIRCUIT, PARTICLE IMAGE ANALYZER, AND STORAGE MEDIUM

This application claims priority under 35 U.S.C. § 119 to Japanese Patent Application No. 2004-253283 filed Aug. 31, 2004, the entire content of which is hereby incorporated by reference.

FIELD OF THE INVENTION

The present invention relates to a method for testing an image processing circuit in which an image processing circuit is tested by executing a predetermined image process of a particle image that contains the image of a particle, a particle image analyzer used in implementing the method for testing an image processing circuit, ands a computer readable storage medium for recording computer programs which allow a computer to function as a particle image analyzer.

BACKGROUND OF THE INVENTION

Particle image analyzers used to manage powder products, mainly fine ceramic particles, pigments, cosmetic powders and the like, are widely known (for example, refer to U.S. Pat. No. 5,721,433). This particle image analyzer encompasses a particle suspension flow with a sheath fluid using a sheath flow cell to convert the flow to a narrow or flat flow, and photographs the particle in the suspension flow to obtain a particle image that contains the image of a particle, so as to acquire information relating to the size and shape of the particle by executing predetermined image processes on the particle image. In general, since a large quantity of images of particles are contained in the particle image, it is desirable to increase the processing speed as much as possible in the particle image analyzer. Therefore, the particle image analyzer is provided with a special built-in image processing circuit board having an image processor (image processing circuit) capable of executing high-speed image processing.

Furthermore, the particle image analyzer is provided with a testing function for testing whether or not a frame memory is writable using the image processor, and testing whether or not the image processor is operating normally.

The previously mentioned conventional particle image analyzer, however, is provided with an image processor having a testing function, and this testing function is independent from the image processing function of the image processor, such that it is necessary to provide a special testing structure (hardware or software) such as a SCAN circuit, BIST (built-in self test) circuit and the like separately from the image processing hardware structure. Accordingly, in order to install the testing function it is necessary to design and develop testing hardware or software completely separately from the image processing hardware, thereby increasing number of development processes and number of design processes.

SUMMARY OF THE INVENTION

The scope of the present invention is defined solely by the appended claims, and is not affected to any degree by the statements within this summary.

In view of the aforesaid information, an object of the present invention is to provide a method for testing an image processing circuit using fewer development processes and design processes than conventional art, and a particle image analyzer and a storage medium recording a computer program used in the implementation of the testing method.

The first aspect of the present invention relates to a method for testing an image processing circuit which executes a predetermined image process on a particle image containing an image of a particle, the method comprising an image processing step for executing the predetermined image process on a test image which contains a test particle image in the image processing circuit; and a testing step for comparing a processing result by the image processing circuit and a predetermined test processing result, and testing whether or not the image processing circuit is functioning normally based on the comparing result.

The second aspect of the present invention relates to a particle image analyzer comprising an image processing circuit for executing a predetermined image process on a particle image containing an image of a particle; an image process executing means for executing the predetermined image process on a test image containing a test particle image in the image processing circuit; and a testing means for comparing the processing result by the image processing circuit and a predetermined test processing result, and testing whether or not the image processing circuit is functioning normally based on the comparing result.

The third aspect of the present invention relates to a particle image analyzer comprising an imaging section for capturing an image of a particle; an image processing circuit for executing a predetermined image process on a particle image containing the image of a particle; a memory for storing beforehand a test image that include a test particle image; an image process executing means for executing the predetermined image process on the test image by the image processing circuit; and a testing means for comparing a processing result by the image processing circuit and a predetermined test processing result, and testing whether or not the image processing circuit is functioning normally based on the comparing result.

The fourth aspect of the present invention relates to a computer readable storage medium for storing a computer program for testing, on a computer, an image processing circuit which executes a predetermined image process on a particle image containing an image of a particle, wherein the computer program comprises an image process execution directing means for directing execution of the predetermined image process using a test image containing a test particle image in the image processing circuit; a reading means for reading, from a memory, a predetermined test processing result recorded beforehand on the memory; and a testing means for comparing the test processing result read by the reading means and a processing result obtained by performing predetermined image process in the image processing circuit, and testing whether or not the image processing circuit is functioning normally based on the comparing result.

DESCRIPTION OF THE PREFERRED EMBODIMENTS

The embodiment of the present invention is described hereinafter with reference to the drawings.

Figure 1:
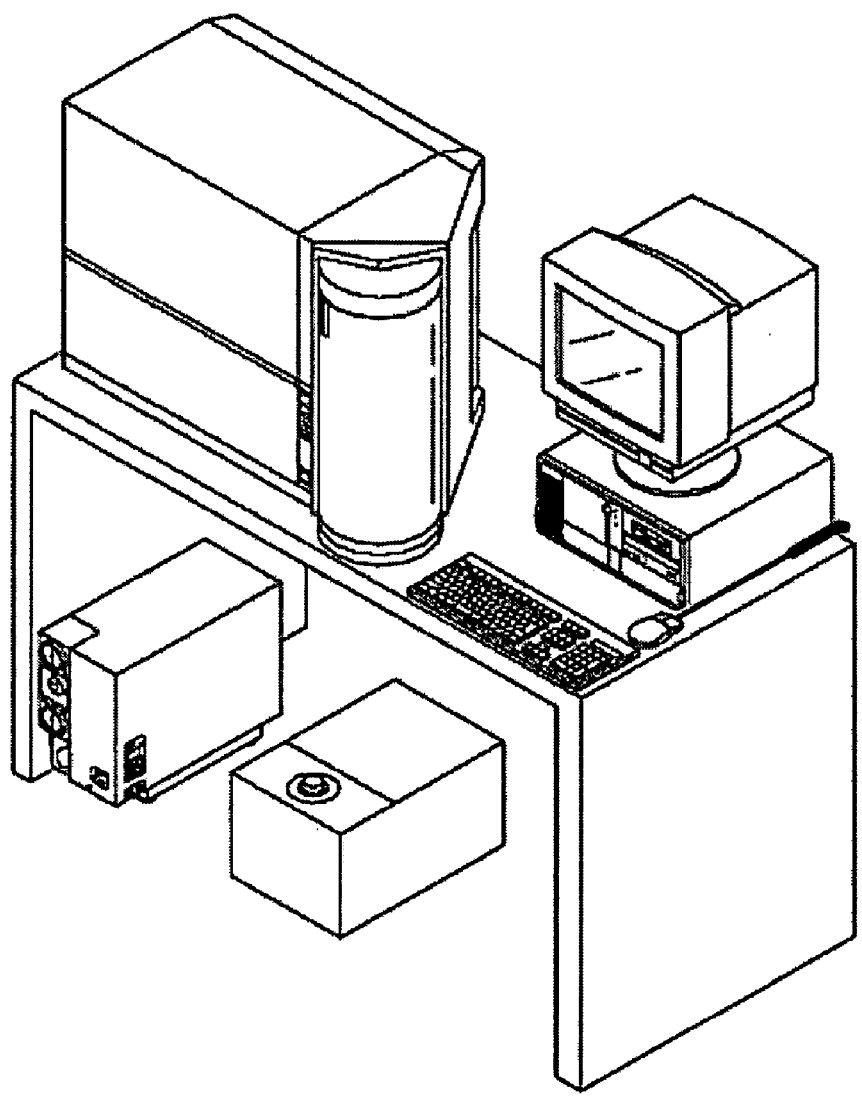
FIG. 1 is a perspective view showing the structure of an embodiment of the particle image analyzer of the present invention.

FIG. 1 is a perspective view showing the structure of an embodiment of the particle image analyzer of the present invention. As shown in FIG. 1, the particle image analyzer 1 of the present embodiment is mainly configured by a measuring unit 2 for capturing a particle image and generating a partial image that include the image of a particle from the particle image, and a data processing unit 3 which is connected to the measuring unit 2 by an electric communication cable (not shown in the drawing) so as to receive the partial image from the measuring unit 2 and analyze the particle by executing image processes on the partial image.

Figure 2:
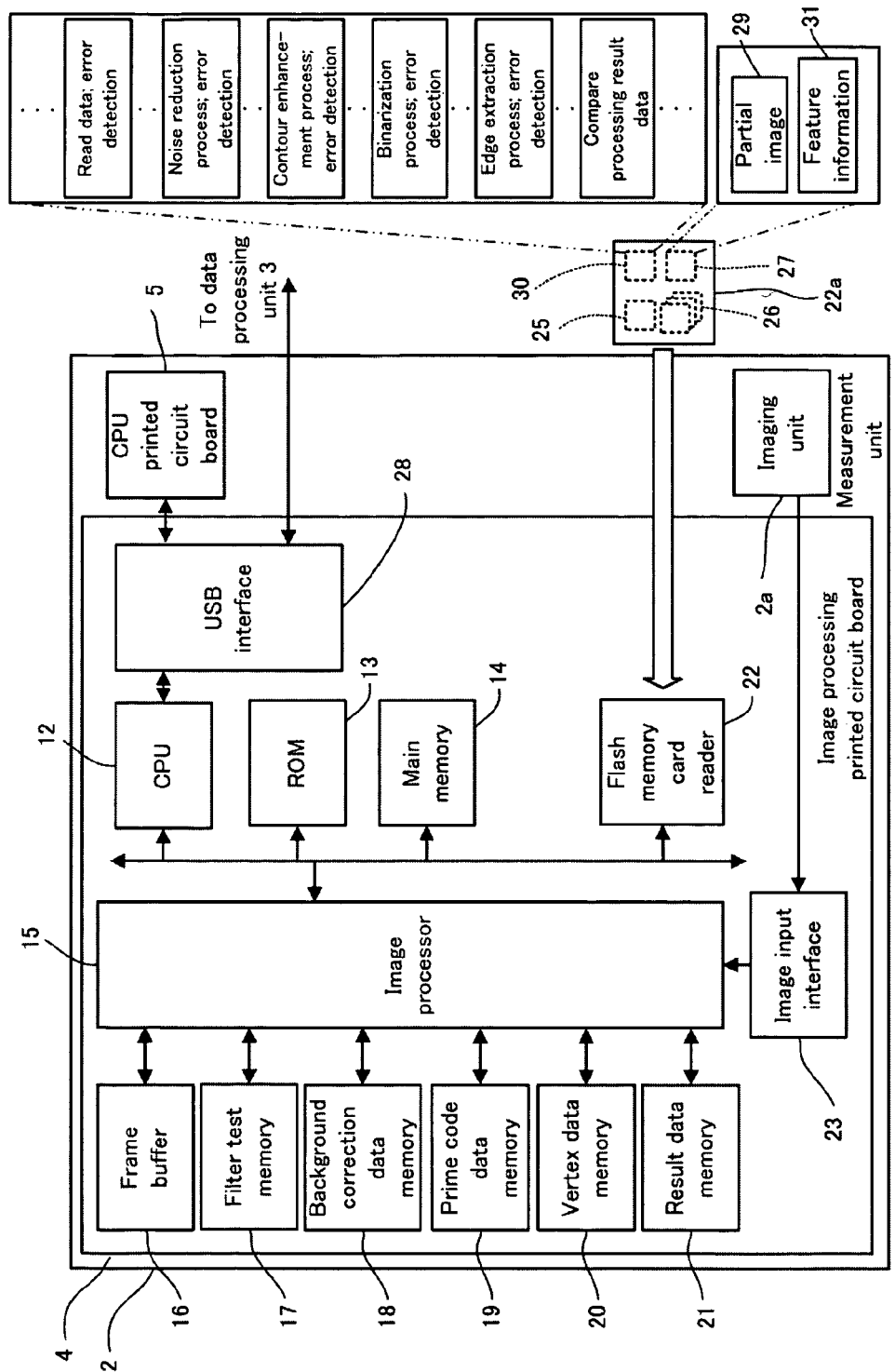
FIG. 2 is a block diagram of the structure of the measuring unit of the particle image analyzer of an embodiment of the present invention.
Figure 3:
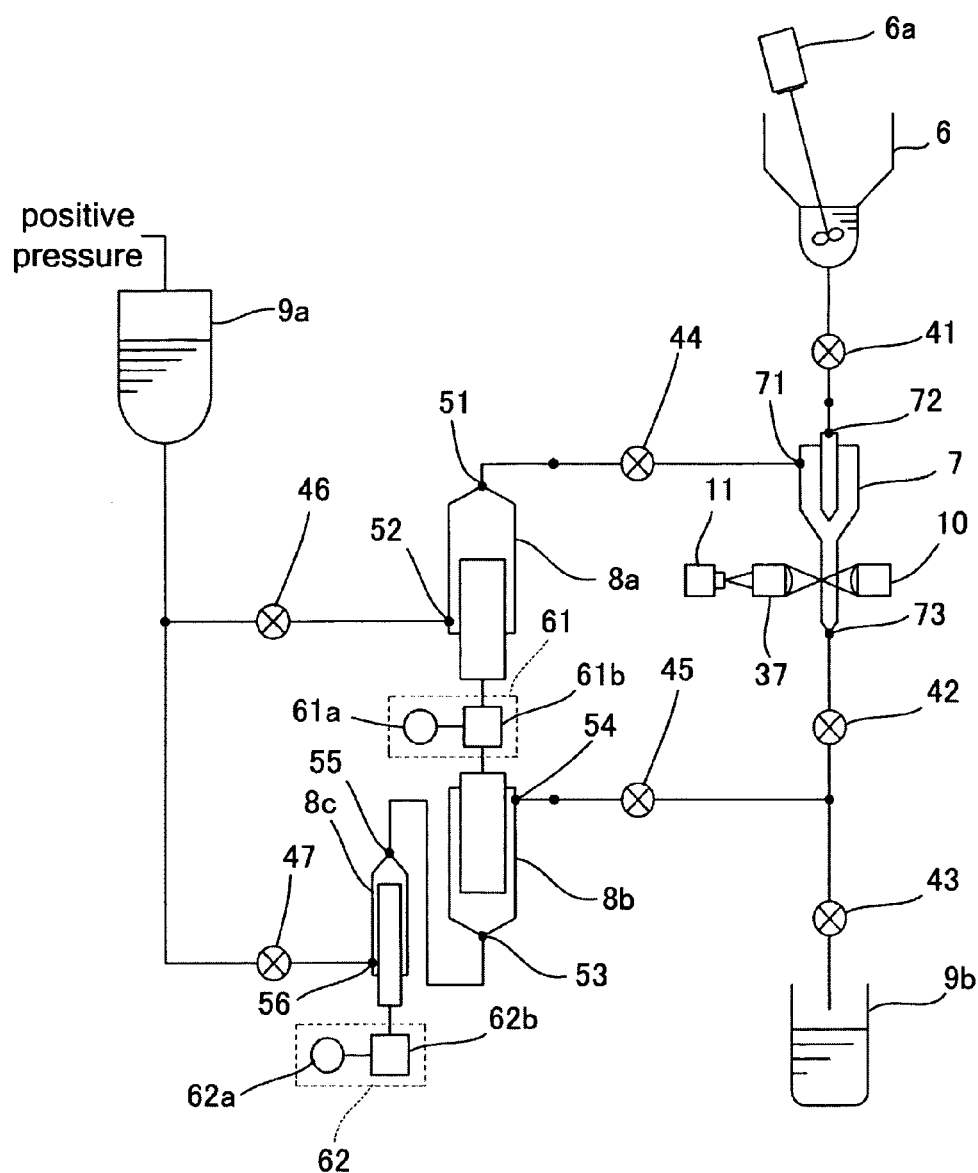
FIG. 3 is a schematic view showing the structure of the imaging unit provided in the measuring unit of the particle image analyzer of the embodiment of the present invention.

FIG. 2 is a block diagram of the structure of the measuring unit of the particle image analyzer of an embodiment of the present invention, and FIG. 3 is a schematic view showing the structure of the imaging unit 2a provided in the measuring unit of the particle image analyzer of the embodiment of the present invention. As shown in FIG. 2, the measuring unit 2 is mainly configured by an imaging unit 2a, image processing printed circuit board 4, and CPU printed circuit board 5.

As shown in FIG. 3, the imaging unit 2a is mainly configured by a sample fluid container 6, sheath flow cell 7, syringe pumps 8a, 8b and 8c, sheath fluid container, waste fluid container 9b, strobe lamp 10, and video camera 11; particle suspension fluid from the sample fluid container 6 is supplied to the sheath flow cell 7, and sheath fluid is fed into the sheath flow cell 7 so as to encapsulate the particle suspension fluid and form a flat suspension fluid flow, and the particles contained in the suspension fluid flow are photographed by the video camera 11.

The structure of the imaging unit 2a is described in detail below. As shown in FIG. 3, the sheath flow cell 7 has a sheath fluid inlet 71, sample fluid inlet 72, and outlet 73 for discharging the sheath fluid and sample fluid mixture. The sample fluid container 6 is constructed such that the top part is open and sample fluid can be accommodated inside, and an outlet is provided in the bottom. The outlet of the sample fluid container 6 is connected to the sample inlet 72 through a flow path. An electromagnetic valve (hereinafter referred to as 'valve') 41 is provided in the flow path between the outlet of the sample container 6 and the sample fluid inlet 72. Furthermore, a mixer 6a is provided to mix the sample fluid in the sample fluid container 6. The sample fluid is a suspension fluid containing particles.

The syringe pump 8a has an outlet 51 and sheath fluid inlet 52. The outlet 51 is connected to the sheath fluid inlet 71 of the sheath flow cell 7 through a flow path. A valve 44 is provided in the flow path between the outlet 51 and the sheath fluid inlet 71. The sheath fluid container 9a is constructed so as to store sheath fluid inside, and an outlet is provided in the bottom. The outlet of the sheath fluid container 9a is connected to sheath fluid inlet 52 through a flow path. A valve 46 is provided in the flow path between the outlet of the sheath fluid container 9a and the sheath fluid inlet 52.

The syringe pump 8b has two outlets 53 and suction ports 54, and the syringe pump 8c has two suction ports 55 and sheath fluid inlets 56. The outlet 53 of the syringe pump 8b is connected to the suction port 55 of the syringe pump 8c through a flow path.

The outlet 73 of the sheath flow cell 7 is connected to the suction port 54 of the syringe pump 8b through a flow path, and the flow path branches from the center, with the branch tip connecting to the opening at the top of the waste fluid container 9b. A valve 42 is provided in the flow path from the outlet 73 to the flow path branching point, and a valve 45 is provided in the flow path from the branching point to the suction port 54. Furthermore, a valve 43 is provided in the flow path between the branching point and opening of the waste container 9b.

The sheath fluid inlet 56 of the syringe pump 8c is connected to the outlet of the sheath fluid container 9a. A valve 47 is provided in the flow path between the outlet of the sheath fluid container 9a and the sheath fluid inlet 56.

The syringe pumps 8a and 8b are driven in linkage by a single first drive source 61, and the syringe pump 8c is driven by a second drive source 62. The first drive source 61 is provided with a stepping motor 61a, and a transmission mechanism 61b for converting the rotational movement of the motor 61a to linear movement which is transmitted to the syringe pumps 8a and 8b. The transmission mechanism 61b is configured by a drive pulley provided on the drive shaft of the stepping motor 61a, and a driven pulley with a timing belt reeved therebetween, such that the rotational movement of the stepping motor 61a is converted to linear movement.

The second drive source 62 is provided with a stepping motor 62a, and a transmission mechanism 62b for converting the rotational movement of the motor 62a to linear movement which is transmitted to the syringe pump 8c. The transmission mechanism 62b is configured by a drive pulley provided on the drive shaft of the stepping motor 62a, and a driven pulley with a timing belt reeved therebetween, such that the rotational movement of the stepping motor 62a is converted to linear movement. The mixer 6a is inserted from the open top into the sample fluid container 6, so as to mix the sample fluid accommodated in the container 6.

Furthermore, the sheath flow cell 7 is provided with a strobe lamp 10 for irradiating the narrowly constricted sample fluid in the sample fluids flow with light, an objective lens 37 and video camera 11 for photographing the particles in the sample fluid.

The structure of the image processing printed circuit board 4 is described below. As shown in FIG. 2, the image processing printed circuit board 4 is mainly configured by a CPU 12, ROM 13, main memory 14, image processor 15, frame buffer 16, filter test memory 17, background correction data memory 18, prime code data memory 19, vertex data memory 20, result data memory 21, flash memory card reader 22, image input interface 23, and USB interface 28. The CPU 12, ROM 13, main memory 14, image processor 15, and flash memory 22 are connected to a bus so as to be mutually capable of data transfers, and the image processor 15, frame buffer 16, filter test memory 17, background correction data memory 18, prime code data memory 19, vertex memory 20, result data memory 21, and image input interface are respectively connected to individual buses. In this way data can be read from the image processor 15 and written to the frame buffer 16, filter test memory 17 background correction data memory 18, prime code data memory 19, vertex data memory 20, and result data memory 21, respectively, and data can be input from the image input interface 23 to the image processor 15.

The CPU 12 is capable of executing computer programs recorded in the ROM 13 and computer programs loaded in main memory 14. This apparatus functions as the particle image analyzer of the present invention when the CPU 12 executes the computer program of the present invention which is described later.

The ROM 13 is a mask ROM, PROM, EPROM, EEPROM or the like, and stores computer programs executed by the CPU 12 and data and the like used by such computer programs.

The main memory 14 is an SRAM, DRAM or the like. The main memory 14 is used when reading the computer program stored in the ROM 13 and flash memory card 22a. The main memory 14 is also used as the work area of the CPU 12 when these computer programs are executed.

The image processor 15 includes special image processing circuits configured in hardware capable of executing image processing such as a median filter process circuit, Laplacean filter process circuit, binarization process circuit, edge tracine process circuit, overlap check circuit, result data generation circuit and the like, and may be configured by FPGA, ASIC and the like.

The frame buffer 16, filter test memory 17, background correction data memory 18, prime code data memory 19, vertex data memory 20, and result data memory 21 are respectively SRAM, DRAM and the like. The memories 16~21 are used for storing data when the image processor 15 executes image processing.

The flash memory card reader 22 is configured so as to be capable of reading data recorded on a flash memory card 22a. The flash memory card 22a has a flash memory (not shown in the drawing) that is capable of saving recorded data even when electric power is not externally supplied. Furthermore, a test image 25, test background image 26, and test result data 27 are stored on the flash memory card 22a.

Figure 4:
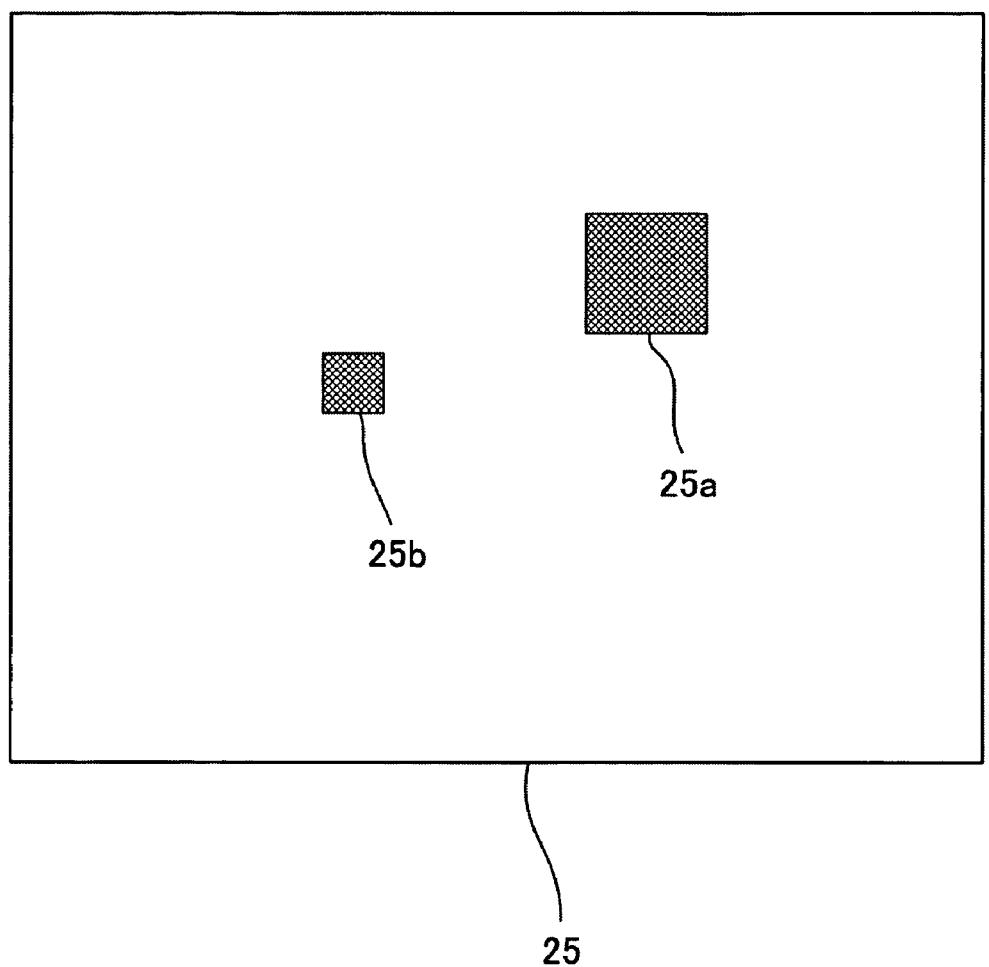
FIG. 4 is a schematic view showing an example of a test image.

The test image 25 is described below. The test image 25 is a monochrome variable contrast image that has the same number of pixels (for example, 512?480 dots) as the particle image generated by the imagining unit 2a, and includes a mock particle image which simulates the image of a particle. FIG. 4 is a schematic view showing an example of a test image. In this example, two square mock particle images 25a and 25b are written in the test image 25. Furthermore, a suitable background is written in the region outside the mock particle images 25a and 25b of the test image 25. This background is omitted to simplify the drawing in FIG. 4. As shown in FIG. 2, a plurality of test background images 26 are stored on the flash memory card 22a. Generally, the same background images as the background images of the test image 25 are written to the respective test background images 26. Furthermore, the test result data 27 is a file that includes test partial image 29 of the mock particle images 25a and 25b, and test feature information (area values of the mock particle images 25a and 25b, linear count number obtained by tracing the edges, slope count number, and corner count number of the mock particle images 25a and 25b) 31 which represents the features of the mock particle images 25a and 25b. The test result data 27 is identical to the data of a file generated by the image processor 15 when the image processes have been executed on the test image 25 during normal operation of the image processor 15.

Furthermore, a self testing computer program 30 of the image processing circuit of the present invention is recorded on the flash memory card 22a. When the particle image analyzer 1 starts operation, the computer program 30 is read from the flash memory card 22a, loaded in the main memory 14, and executed by the CPU 12. The particle image analyzer 1 operates in the manner described below through the execution of the computer program 30 by the CPU 12.

The image input interface 23 is provided with a video digitizing circuit (not shown in the drawing) that includes an A/D converter. The image input interface 23 is electrically connected to the video camera 11 by an electrical signal cable, such that progressive video camera signals, for example, 640?480 dots per frame, can be received at 60 fps from the video camera 11. The video signals input from the video camera 11 are subjected to A/D conversion by the image input interface 23. The digitized image data (particle image) are stored in the frame buffer 16.

The image processing printed circuit board 4 is connected to a USB interface 28 through a PCI bus. The USB interface 28 is connected to the CPU printed circuit board 5 through a USB/RS-232C converter which is not shown in the drawing. The CPU printed circuit board 5 is provided with a CPU, ROM, RAM and the like, and all controls of the measuring unit 2 are performed by the CPU printed circuit board 5. The USB interface 28 is connected to the data processing unit 3 by a USB cable.

The data processing unit 3 is configured by a personal computer, and includes a body provided with a display device, CPU, ROM, RAM, hard disk and the like, and an input device that includes a keyboard and mouse. An operating system, and application programs for communicating with the measuring unit 2, and performing predetermined analyses based on the measurement results of the measuring unit 2 are installed on the hard disk, such that the personal computer functions as a data processing unit 3 when the CPU executes the application programs over the operating system.

The operation of the particle image analyzer 1 of the present embodiment of the invention is described below. The operation of the particle image analyzer 1 of the present embodiment can be broadly divided into a self testing operation at startup, and a normal running operation after the apparatus has been tested and determined to be operating normally by the self testing operation. The normally running operation is described first below.

In normal running operation, initially, the syringe pump 8a is set with the piston pulled from the syringe (dischargeable state), and the syringe pump 8b is set with the piston pushed into the syringe (suctionable state), in FIG. 3. The syringe pump 8c is also set in a suctionable state. These states are the initial states. Furthermore, all the valves 41~47 are closed in the initial state.

Then, from the initial state, the valves 42, 43, 44, and 46 are opened. A positive pressure is applied beforehand to the sheath fluid container 9a, such that sheath fluid is pushed from the container 9a passes through the valve 46, syringe pump 8a, valve 44, sheath flow cell 7, and valves 42 and 43 to the waste container 9b. In this way the flow path is cleaned from the sheath fluid container 9a through the valve 46, syringe pump 8a, valve 44, sheath flow cell 7, and valves 42 and 43 to the waste container 9b. Then, the valves 42, 43, 44, and 46 are reclosed. Thus, sheath fluid is loaded in the syringe pump 8a.

Then, the valves 43, 45, and 47 are opened. Sheath fluid is pushed from the container 9a through the syringe pump 8c, syringe pump 8b, and valves 45 and 43 to the waste container 9b. In this way the flow path is cleaned from the sheath fluid container 9a through the syringe pump 8c, syringe pump 8b, and valves 45 and 43 to the waste container 9b. Then, the valves 43, 45, and 47 are reclosed. Thus, sheath fluid is loaded in the syringe pumps 8b and 8c.

Next, the valves 41, 42, 44, and 45 are opened, and the stepping motors 61a and 62a are actuated. In this way the syringe pump 8a operates to discharge an amount Q, and the syringe pump 8b operates to suction an amount Q in conjunction therewith, and the syringe pump 8c suctions an amount Qs.

Figure 5:
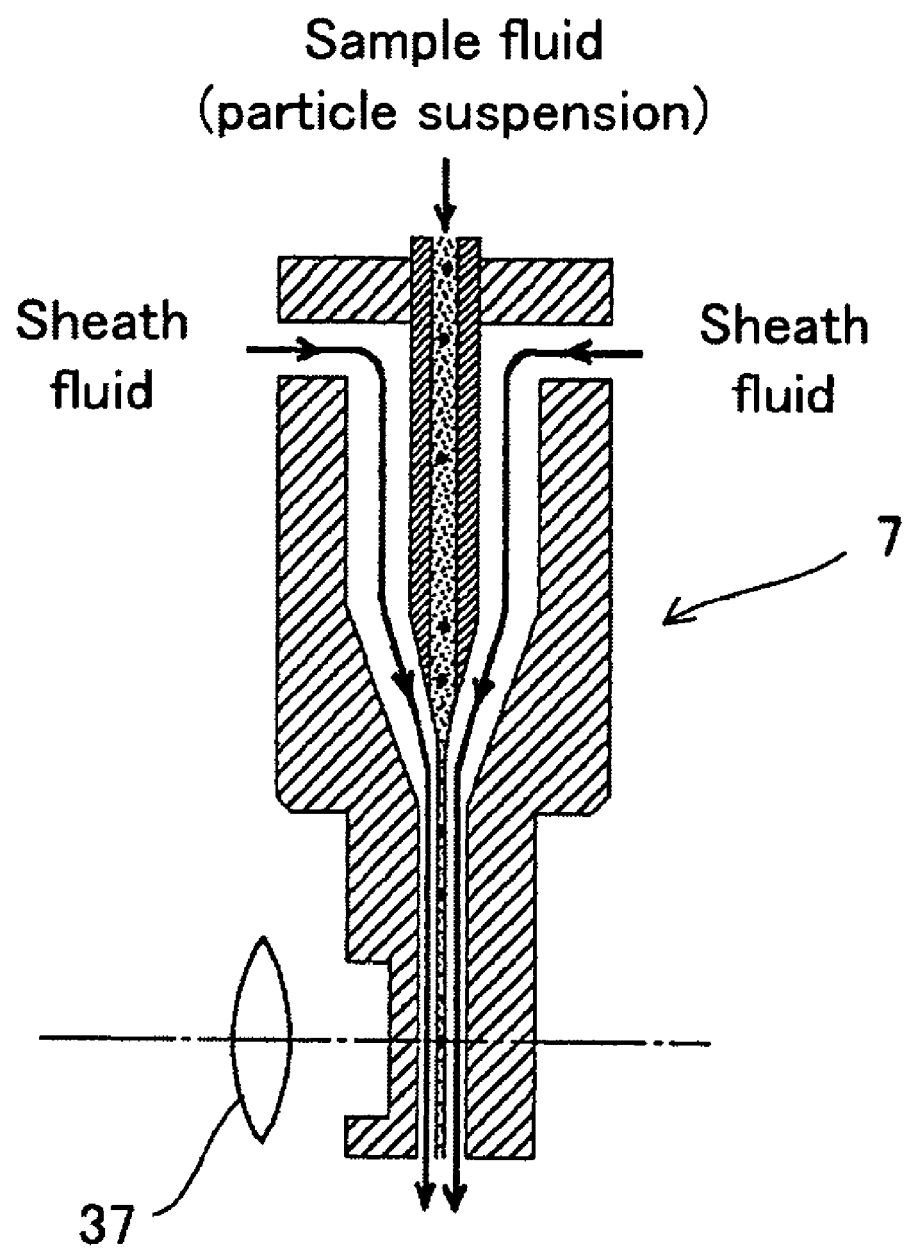
FIG. 5 is a cross section enlargement of the sheath flow cell of FIG. 3.

FIG. 5 is a cross section enlargement of the sheath flow cell of FIG. 3, and shows the condition in which a flat suspension flow is formed by the sheath flow cell 7. By means of this operation, an amount Q of sheath flow from the syringe pump 8a, and an amount Qs of sample fluid (particle suspension fluid) from the sample container 6 are introduced together into the sheath flow cell 7. Then, the sample fluid is encapsulated in the sheath fluid, and a narrowly constricted suspension fluid flows within the sheath flow cell 7 and mixes with the sheath fluid to form a mixture in the amount (Q+Qs), which is discharged from the sheath flow cell 7, as shown in FIG. 5.

Within the discharged mixture, an amount Q of the mixture is suctioned by the syringe pump 8b, and an amount Qs of the mixture is suctioned by the syringe pump 8c. At this time a pulse light from the strobe lamp 10 periodically irradiates the flat constricted suspension flow every 1/60 of a second, and every 1/60 of a second a still image of the particles is captured by the video camera 11 through the objective lens 37.

When the measurement particles are in a semitransparent condition, it is desirable that a suitable stains is applied to the particles. Although not shown in FIG. 3, a stain bottle may be provided within the apparatus, and a reaction chamber may be added to stain the sample with the stain.

An optimum medium for dispensing the particles may be selected in accordance with the characteristics (particle diameter and specific gravity) of the particles. Furthermore, it is desirable to change the viscosity and specific gravity of the sheath fluid in accordance with the characteristics of the sample fluid, for example, the viscosity and specific gravity of the medium, to reliably flatten or narrowly constrict the flow of the sample fluid. Although not shown in FIG. 3, a plurality of types of sheath fluid containers may be provided, and a mechanism added to easily switch the type of sheath fluid used in accordance with the measurement sample.

If the flat surface of the suspension fluid is photographed by the video camera 11, a particle image can be captured along the entire photographic area of the video camera 11, and a plurality of particles can be photographed by a single photograph. Furthermore, since the distance between the center of the photographed particle and the imaging surface of the video camera 11 can be made constant, particle images can be obtained which are normally focused regardless of the size of the particle. Furthermore, the direction of flat particles and narrow particles can be easily managed, such that the characteristics parameters for analyzing particles can minimize variations with excellent reproducibility.

When the suspension fluid is flattened, the number of images of particles photographed by a plurality of pulse light irradiations is determined by the surface area of the imaging surface of the video camera 11, thickness of the sample flow, number of particles per unit volume of the sample fluid, and number of images (number of frames). For example, 3600 particles can be photographed when the imaging area is 200?200 ?m, sample flow thickness is 5 ?m, particle density is 10,000/?1, and number of frames is 1800 (photography time of 30 seconds).

The imaging surface area is determined by the imaging ratio and size relative to the photoreceptor surface of the video camera 11. The larger the magnification of the objective lens 37, the smaller is the imaging area, although small particles can be photographed larger. The smaller the magnification of the objective lens 37, the larger is the imaging area, which is suitable for photographing large particles. In this apparatus, the magnification of the objective lens 37 is selectable, or switchable during measurement (not shown in the drawings), to increase the particle size measurement range.

Thus, still images (particle images) taken by the video camera 11 are output to the image processing printed circuit board 4 as video signals. The received video signals are subjected to A/D conversion in the image input interface 23 of the image processing printed circuit board 4 to generate digital image data. Then, the image process described below are executed.

Figure 6:
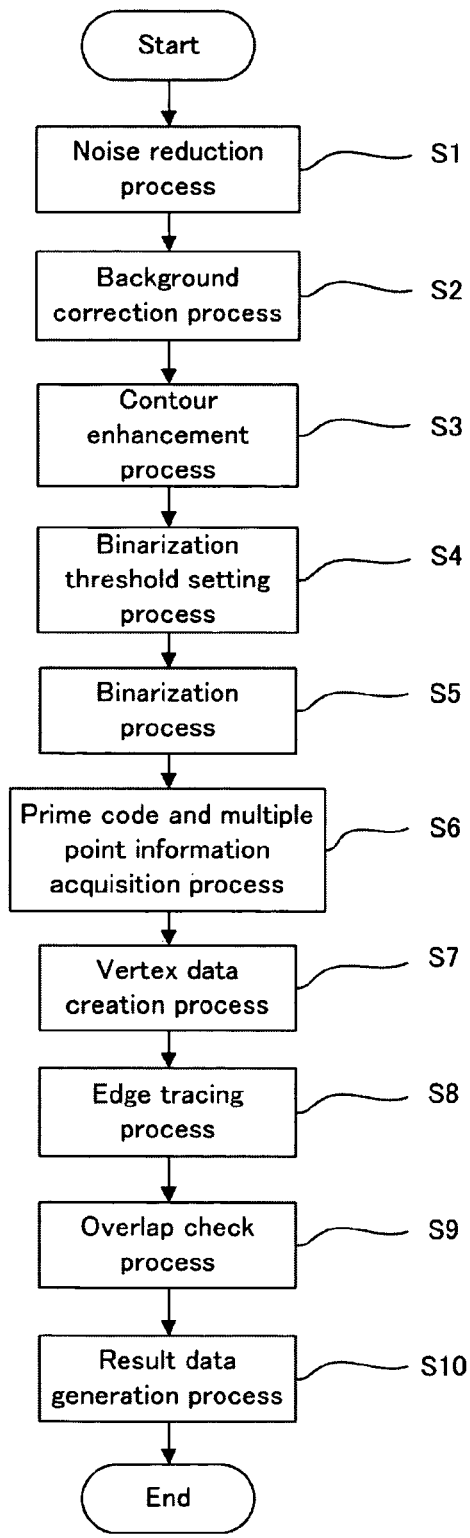
FIG. 6 is a flow chart showing the processing flow of the image processor in the normal running operation of the particle image analyzer of the embodiment of the present invention.

FIG. 6 is a flow chart showing the processing flow of the image processor in the normal running operation of the particle image analyzer 1 of the embodiment of the present invention. Image data output from the image input interface 23 are stored in the frame buffer 16 by DMA transfer. The image processor 15 executes a noise reduction process on the particle image stored in the frame buffer 16 (step S1). The noise reduction process S1 is described in detail below. A median filter process circuit is provided in the image processor 15, and a median filter process is executed by the median filter process circuit in the noise reduction process S1. The median filter process sorts the various luminance values (pixel values) of nine pixels including a target pixel and eight adjacent pixels, and sets the median (middle value) as the pixel value of the target pixel.

Next, the image processor 15 executes the background correction process to correct variation (shading) in the intensity of the light irradiating the suspension fluid (step S2). The background correction process S2 is described in detail below. Before supplying suspension fluid to the flow cell 9, sheath fluid alone is supplied to the flow cell 9 and particles do not pass through the flow cell 9, and at this time data of a plurality of images is acquired by light irradiation and captured by the image processing printed circuit board 4, and from these image data is generated a background correction image that is stored in the background correction data memory 18. The process for generating the background correction image is executed by the CPU 12 directly before the measurement of the particles each time particle measurement is performed. The background correction image is an image that matches an image with only background and from which the images of particles have been removed. As described previously, a Laplacean filter process circuit is provided in the image processor 15, and in the background correction process S2, the Laplacean filter process circuit compares the background correction image and the median filter processed images of particles, and generates a correction image from which the images of particles from which the background is generally removed.

Figure 7:
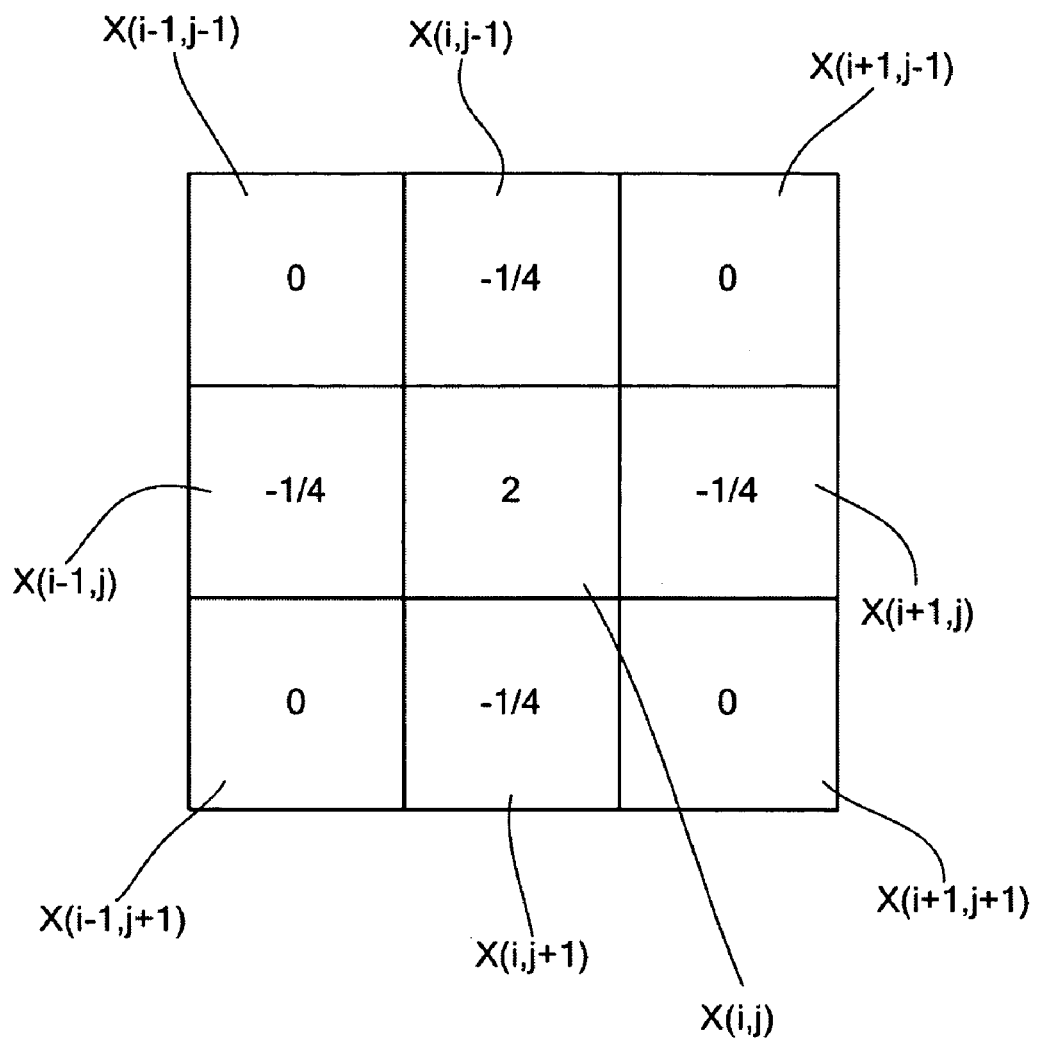
FIG. 7 is a schematic view illustrating the setting values of coefficients in the present embodiment.

Next, the image processor 15 executes a contour enhancement process (step S3). The contour enhancement process S3 is described in detail below. In the contour enhancement process S3, a Laplacean filter process is performed by the Laplacean filter process circuit. The Laplacean filter process multiplies the various luminance values (pixel values) of nine pixels including a target pixel and eight adjacent pixels by predetermined coefficients corresponding to the luminance value, and sets the sum of the multiplication results as the pixel value of the target pixel. FIG. 7 is a schematic view illustrating the setting values of coefficients in the present embodiment. As shown in FIG. 7, in the present embodiment a coefficient of 2 corresponds to a target pixel X (*1, j), a coefficient of ?1/4 corresponds to the four adjacent pixels X(i, j−1), X(i−1, j), X(i+1, j), X(i, j+1) above and below and to left and right of the target pixel, and a coefficient of 0 corresponds to the four pixels X(i−1, j−1), X(i+1, j−1), Xi−1, j+1), and X(i+1, j+1) adjacent in diagonal directions from the target pixel. The pixel value Y(i, j) of the target pixel after the filter process is calculated by equation (1) below. When the calculation result exceeds 255, 255 is output, and 0 is output when the calculation results in a negative number.

The image processor 15 then sets a binarization threshold level based on the data after the process of the contour enhancement process S3. This process sis described in detail below. A luminance histogram unit is provided in the Laplacean filter process circuit of the image processor 15, and the process of step S4 is executed by the luminance histogram unit. First, the image processor 15 creates a luminance histogram from the image data after the Laplacean filter process, and the obtained luminance histogram is subjected to a predetermined smoothing process. Then, mode of the luminance values is determined from the smoothed luminance histogram, and a binarization threshold is calculated using this luminance mode value and equation (2) below.

$$\text{Binarization threshold} = \text{Luminance mode value} \; ?A + B \quad (2)$$

In equation (2) A and B are settable parameters; in the present embodiment, default values are A=90, and B=0.

Figure 8:
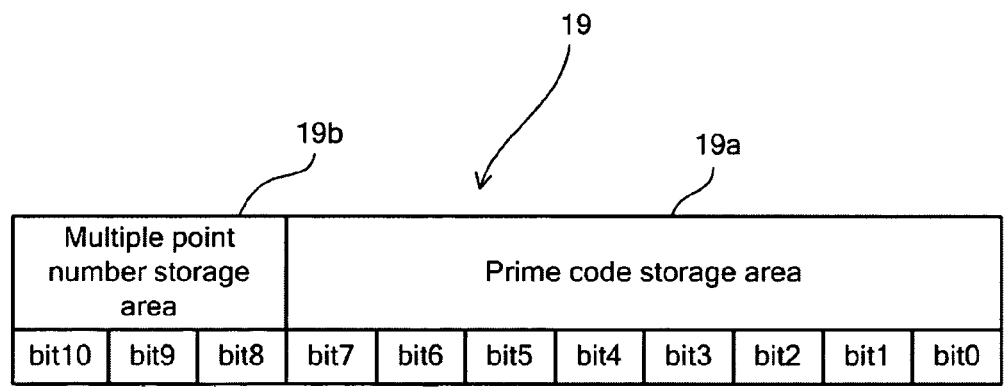
FIG. 8 is a schematic view showing the content of the prime code data storage memory.
Figure 9:
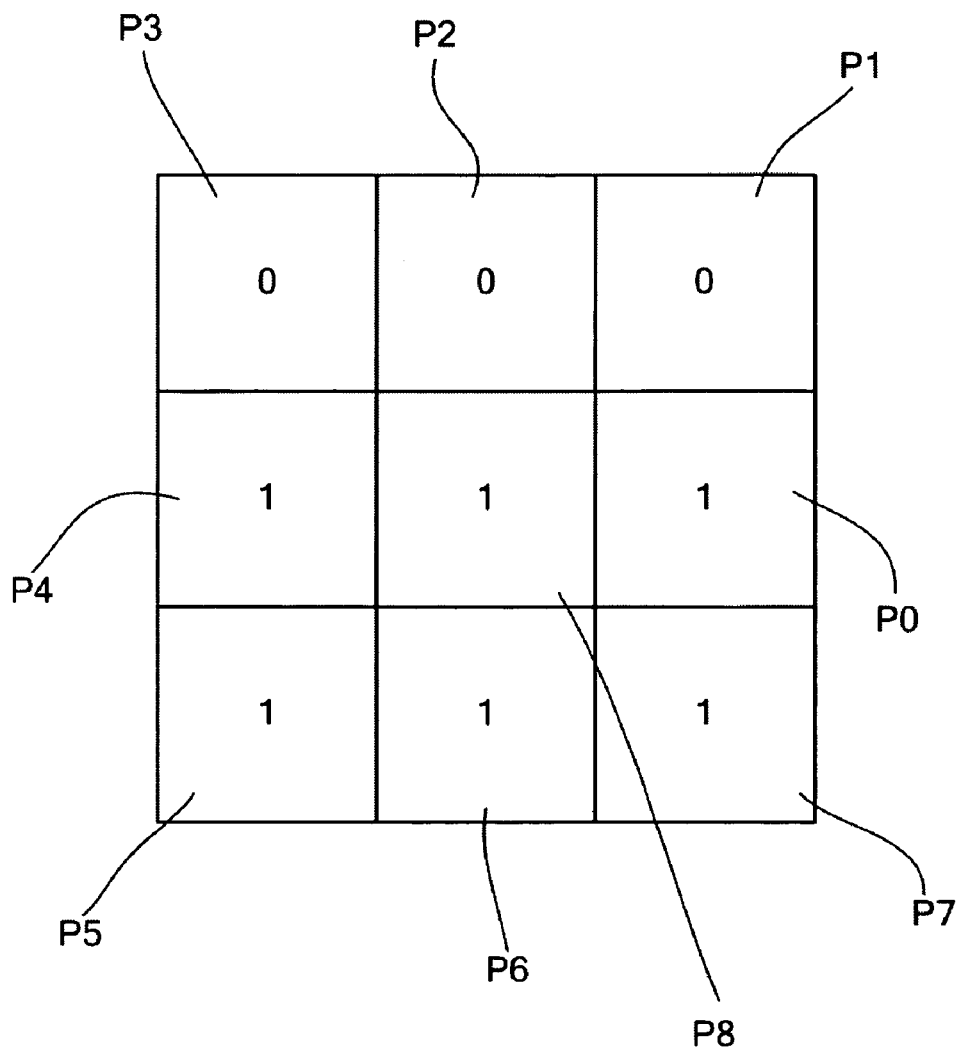
FIG. 9 is a schematic view illustrating the prime code definitions.

Then, the image processor 15 performs a binarization process on the image after the Laplacean filter process, at the threshold level set in the process of step S4. Next, the prime code and multiple point information are acquired for each pixel of the binarized image. The processes of steps S5 and S6 are described in detail below. As previously described the image processor 15 is provided with a binarization process circuit, and this binarization process circuit executed the processes of steps S5 and S6. The prime codes are binary codes determined for nine pixels, that is, the target pixel and eight adjacent pixels, and are defined below. FIG. 8 is a schematic view showing the content of the prime code data storage memory 19. FIG. 8 shows the structure of one word in the prime code data memory 19. As shown in FIG. 8, the prime code data memory 19 contains two regions, prime code storage region 19*a* and multiple point storage region 19*b*, in one word (11 bits). The prime code storage region 19*a* is an 8-bit region representing bit 0 through bit 7, and multiple point storage region 19*b* is a 3-bit region representing bit 8 through bit 10. The prime code definition is described below. FIG. 9 is a schematic view showing an example of pixel values in a 3?3 pixel region of the binary image data. As shown in FIG. 9, regarding the nine pixels of binary image data P0~P8, the image data P1~P3 become 0, and P0 and P4~P8 become 1. The prime codes in this case are described below. Excluding the target pixel P8, the pixels P0~P7 correspond bit 0 through bit 7 of the prime code storage region 19*a*. That is, the prime code storage region 19*a* stores pixel values of pixels P0~P7 from the low order bit to the high order bit. That is, the prime codes in this case are 11110001 in binary numerals, and F1 in hexadecimal notation. Furthermore, the pixel value of the target pixel P8 is not included in the prime codes.

Figure 10:
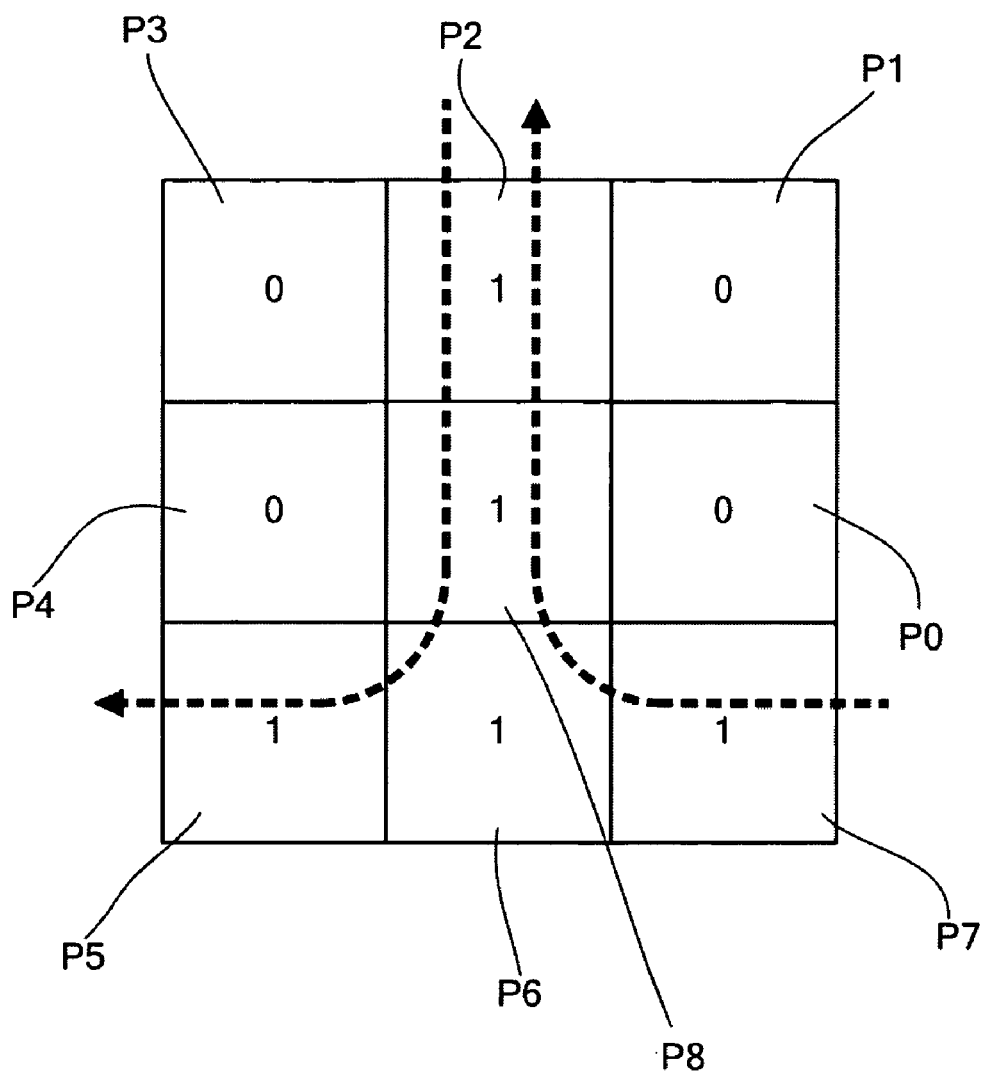
FIG. 10 is a schematic view illustrating the multiple point concept.

Multiple point information is determined when the region formed by the target pixel and eight adjacent pixels are part of the border of an image of a particle, that is, when the prime code is other than 00000000. Multiple points are codes indicating whether or not there is a possibility multiple passes during edge tracing; multiple point information corresponding to all patterns are recorded beforehand in a lookup table, and multiple points are determined by referencing this lookup table. FIG. 10 is a schematic view illustrating the multiple point concept. In the example shown in FIG. 10, the pixel values of pixels P2, and P5~P8 is 1, and the pixel values of the other pixels P0, P1, P3 and P4 is 0. In this case, there is a possibility of two pass-throughs at pixel P8 during edge tracing, as indicated by the arrows in the drawing. Therefore, in the example of FIG. 10, the target pixel P8 has two point, and the number of multiple points is 2. The number of multiple points is stored in the multiple point storage region 19*b*.

Then, the image processor 15 prepares vertex data (step S7). The process of step S7 is also executed by the binarization process circuit. Vertex data are data representing the predetermined coordinates for starting the subsequent edge tracing. The determination of a vertex is restricted to patterns which match all three conditions below in which the nine pixel region including a target pixel and eight adjacent pixels is set such that (1) the pixel value of the target pixel P8 is 1, (2) the pixel values of P1~P4 (the three pixels above and one pixel to the left of the target pixel) is 0, and (3) the pixel values of at least one among the four pixels P5~P7 (the three pixels below and one pixel to the right of the target pixel) is 1. The image processor 15 searches pixels equivalent to a vertex among all pixels, and stores the created vertex data (coordinate data representing the position of a vertex) in the vertex data memory 20.

The image processor 15 then executes the edge tracing process (step S8). The edge tracing process S8 is described in detail below. As previously mentioned, an edge tracing process circuit is provided in the image processor 15, and the edge tracing process S8 is executed by the edge tracing process circuit. In the edge tracing process S8, first, coordinates are specified for starting the edge tracing from the vertex data, and edge tracing of the image of a particle is performed based on the prime codes from the coordinates and codes for determining the advancing direction specially recorded beforehand. Then, during edge tracing, the image processor 15 calculates the surface area, linear count number, slope count number, corner count number, and position of each image of a particle. The surface area of the image of a particle is the total number of pixels constituting the image of the particle, that is, the total number of pixels contained within the region circumscribed by the edges. Furthermore, the linear count number is the total number of edge pixels excluding edge pixels at both ends of a linear section when three or more edge pixels of an image of a particle are arrayed linearly in a vertical or horizontal direction, that is, the total number of edge pixels constituting a linear component extending vertically or horizontally among the edges of the image of a particle. The slope count number is the total number of edge pixels excluding edge pixels at both ends of a linear section when three or more edge pixels of an image of a particle are arrayed linearly in a sloping direction, that is, the total number of edge pixels constituting a linear component extending in a sloping direction. The corner count number is the total number of a plurality of edge pixels in contact from different directions (for example, one edge pixel adjacent above, and another edge pixel adjacent to the left) among the edge pixels of an image of a particle, that is, the total number of edge pixels configuring a corner among the edge pixels of an image of a particle. The position of the image of a particle is the coordinates, for example, of the right end, left end, top end, and bottom end of the image of the particle. The image processor 15 stores the calculation result data in an internal memory (not shown in the drawing) built into the image processor 15.

Figure 11:
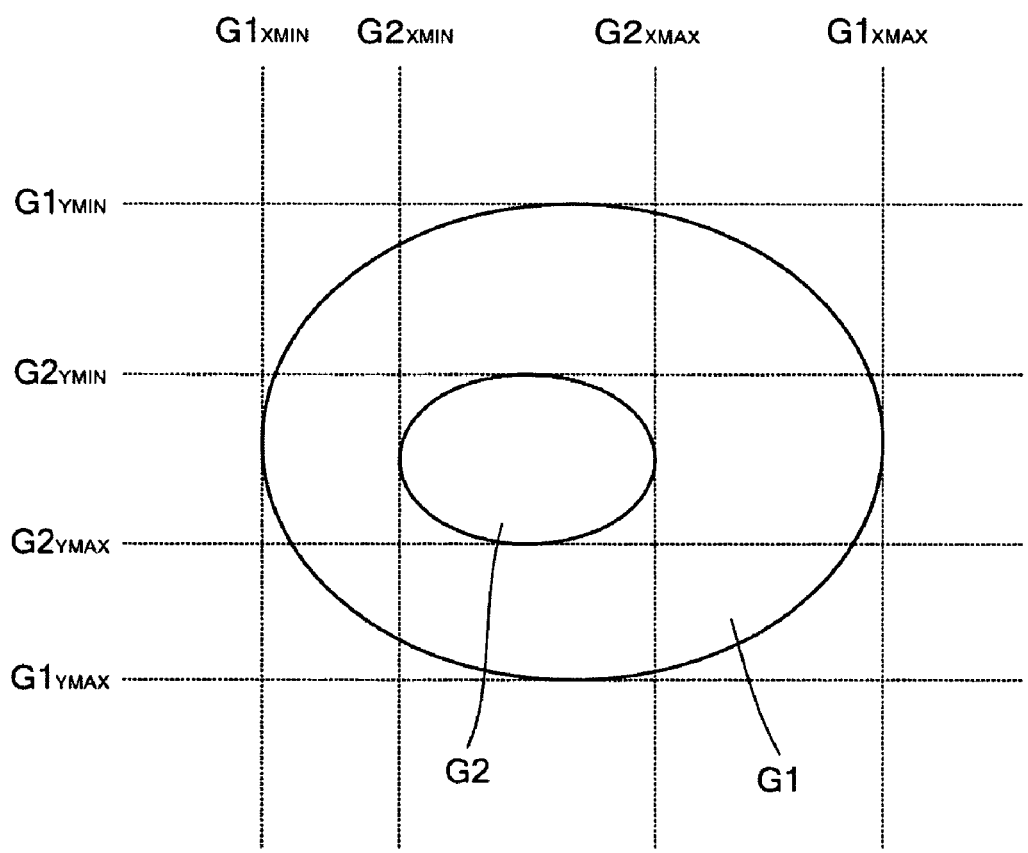
FIG. 11 is a schematic view illustrating the principle for determining whether or not an inside particle image is present.

The image processor 15 then executes the particle overlap check process (step S9). The particle overlap check process S9 is described in detail below. As previously mentioned, the image processor 15 is provided with an overlap check circuit, and the overlap check process S9 is executed by this overlap check circuit. In the overlap check process S9, the image processor 15 determines whether or not another image of a particle (hereinafter referred to as 'inside particle image') is included within the image of one particle (hereinafter referred to as 'outside particle image') based on the analysis result of the image of a particle in the previously described edge tracing process S8, and, when an inside particle image is present, excludes the inside particle image from the extracted object of the image of the particle in the subsequent result data creation process S10. The principle for determining whether or not an inside particle image is present is described below. FIG. 11 is a schematic view illustrating the principle for determining whether or not an inside particle image is present. First, as shown in FIG. 11, two images of particles are selected, and the maximum value $G1_{XMAX}$ and minimum value $G1_{XMIN}$ (horizontal direction coordinates) of the X coordinates and the maximum value $G1_{YMAX}$ and minimum value $G1_{YMIN}$ (vertical direction coordinates) of the Y coordinates are specified for one particle image G1, and the maximum value $G2_{XMAX}$ and minimum value $G2_{XMIN}$ of the X coordinates and the maximum value $G2_{YMAX}$ and minimum value $G2_{YMIN}$ of the Y coordinates are similarly specified for the other particle image G2. Then, when the following four conditions are satisfied, the particle image G1 is determined to contain the particle image G2.

(1) $G1_{XMAX}$ is greater than $G2_{XMAX}$.
(2) $G1_{XMIN}$ is less than $G2_{XMIN}$.
(3) $G1_{YMAX}$ is greater than $G2_{YMAX}$.
(4) $G1_{YMIN}$ is less than $G2_{YMIN}$.

The result data of the overlap check process are stored in the internal memory of the image processor 15.

The image processor 15 extracts partial images separately include previously specified images of particles from the particle image, and creates image processing result data (step S10). As described above, the image processor 15 is provided with a result data creation circuit, and the result data creation process S10 is executed by the result data creation circuit. The partial images generated by this process are images, extracted from a particle image, of square regions including a margin region determined by blank values set beforehand of one image of a particle. The image processing result data include data of partial images, positions of images of particles, surface areas of images of particles, linear count number, slope count number, and corner count number of all images of particles recognized by the previously described image process. Furthermore, the image processor 15 stores the image processing result data generated by the aforesaid process in the result data memory 21. Thus, the image process by the image processor 15 ends. The image processor 15 repeatedly executes the aforesaid image process by pipeline processing, and generates a partial image of each frame.

In this way the image processing result data stored in the result data memory 21 are transferred through the USB interface 28 to the data processing unit 3 by DMA transfer. The data processing unit 3 executes image process on the partial images included in the received image processing result data, and calculates the size (circle-equivalent diameter) and degree of roundness of the image of the particle. Then, the received partial images are displayed arranged in a matrix pattern on the display screen, and the size and degree of roundness of a particle of a selected partial image is displayed.

Figure 12:
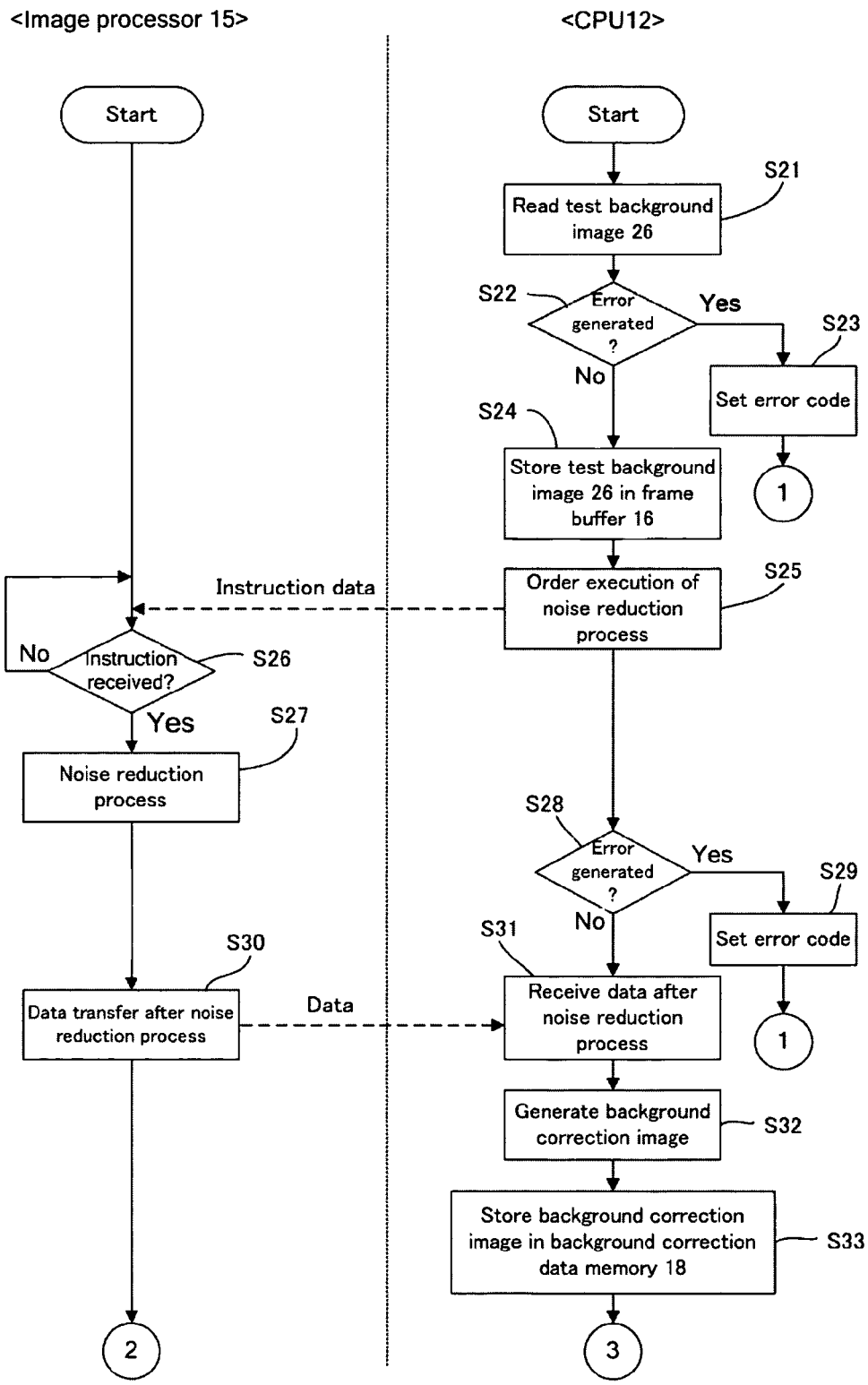
FIG. 12 is a flow chart showing the processing sequence of the CPU and the image processor during the self testing operation of the particle image analyzer of the embodiment of the present invention.
Figure 13:
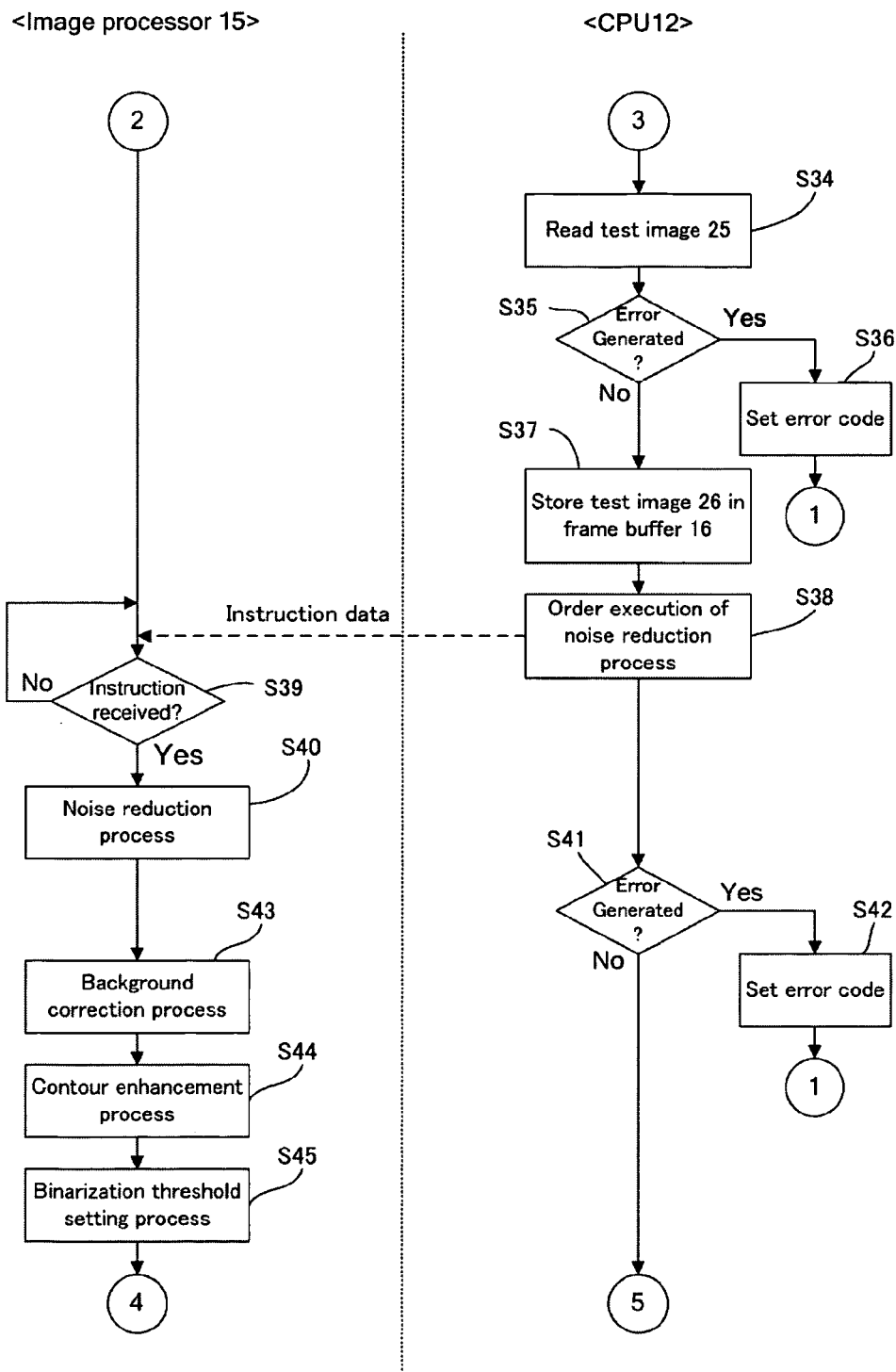
FIG. 13 is a flow chart showing the processing sequence of the CPU and the image processor during the self testing operation of the particle image analyzer of the embodiment of the present invention.
Figure 14:
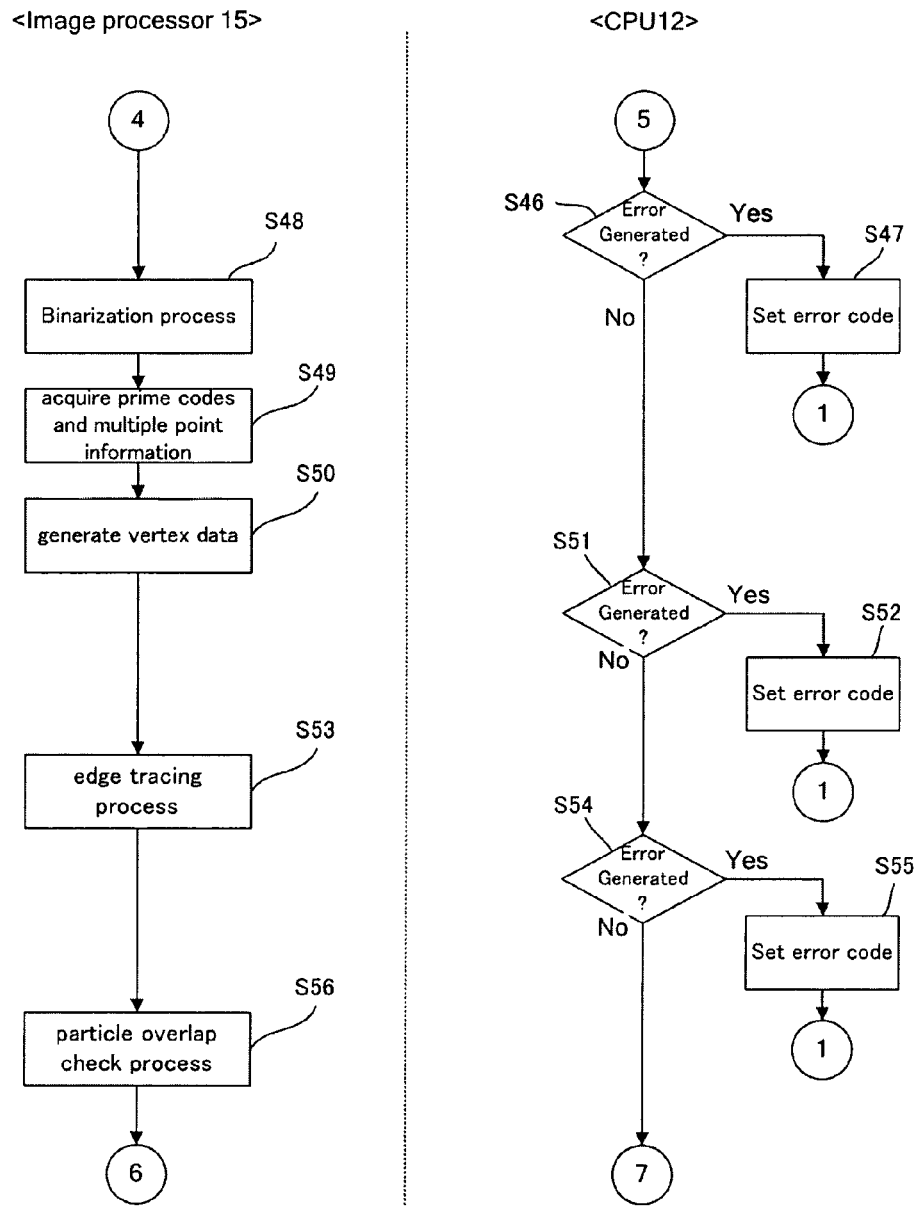
FIG. 14 is a flow chart showing the processing sequence of the CPU and the image processor during the self testing operation of the particle image analyzer of the embodiment of the present invention.
Figure 15:
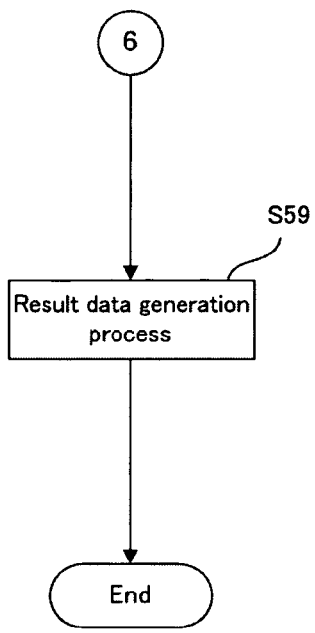
FIG. 15 is a flow chart showing the processing sequence of the CPU and the image processor during the self testing operation of the particle image analyzer of the embodiment of the present invention.
Figure 15:
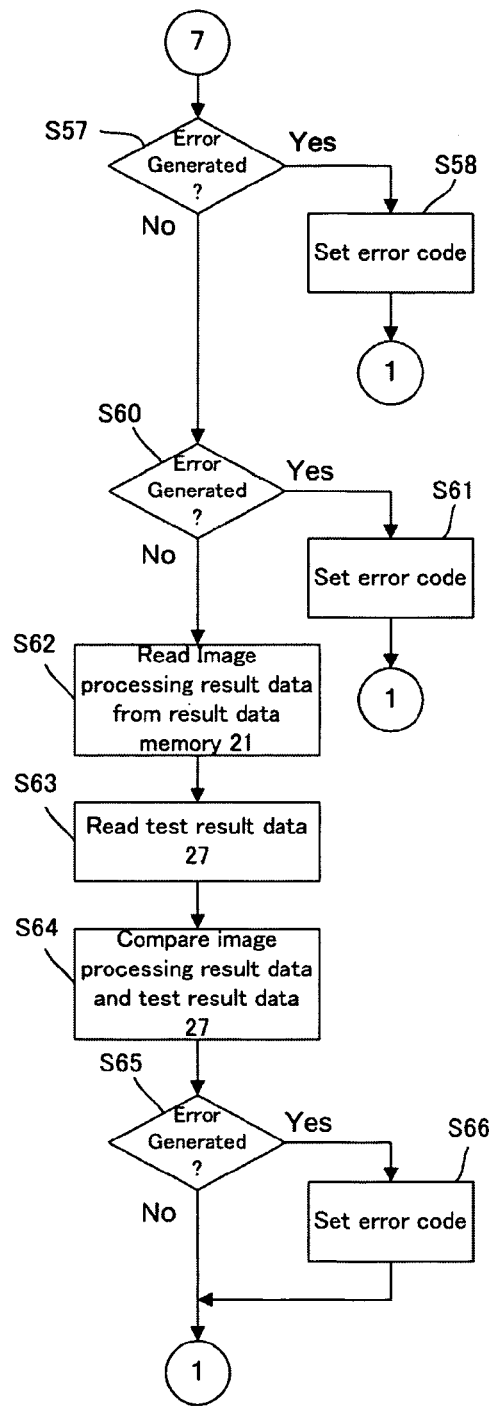
Figure 16:
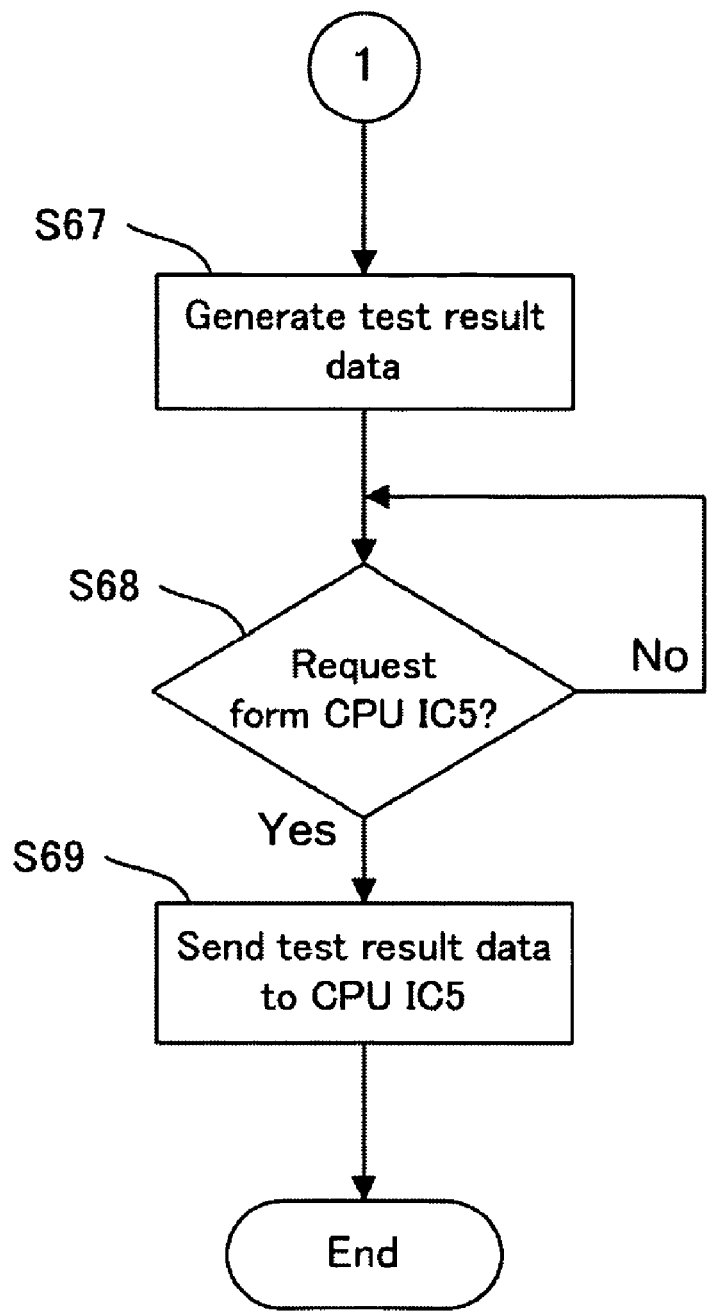
FIG. 16 is a flow chart showing the processing sequence of the CPU and the image processor during the self testing operation of the particle image analyzer of the embodiment of the present invention.

The self testing operation of the particle image analyzer 1 of the present embodiment of the invention is described below. The self testing operation is performed at startup of the particle image analyzer 1, and a determination is made as to whether or not the image processor 15 of the particle image analyzer 1 is operating normally. FIG. 12 is a flow chart showing the processing sequence of the CPU 12 and the image processor 15 during the self testing operation of the particle image analyzer 1 of the embodiment of the present invention. The flash memory card reader 22 reads a plurality of test background images 26 stored on the flash memory card 22a, and the CPU 12 receives the data. The CPU 12 determines whether or not an error has been generated when the data are read by the flash memory card reader 22 (step S22). Such errors include failed access errors in which the flash memory card reader 22 fails to access the flash memory card 22a, data reading errors by the flash memory card reader 22 and the like. When an error is detected (step S22: YES), the CPU 12 sets an error code associated beforehand to the error, that is, the error code is stored in a predetermined region of the main memory 14 (step S23), and the process moves to step S67. In this way malfunction of the flash memory card reader 22 or flash memory card 22a, or errors such as no data present on the flash memory card 22a and the like can be detected by determining whether or not data are read normally by the flash memory card reader 22. That is, when an abnormality is detected, it is possible to specify whether the location of the abnormality of the flash memory card reader 22 or the flash memory card 22a.

When an error is not detected in step S22 (step S22: NO), the CPU 12 stores the data of a plurality of test background images 26 in the frame buffer 16 (step S24). Then, the CPU 12 instructs the image processor 15 to execute the noise reduction process (step S25). The image processor 15 awaits an instruction to execute the noise reduction process (step S26), and when such instruction is received (step S26: YES), the previously mentioned noise reduction process is executed on the test background images 26 stored in the frame buffer 16 (step S27). At this time the image processor 15 sets status information indicating the currently executing/standby noise reduction process to an internal status register (not shown in the drawing), and the CPU 12 determines whether or not an error has been generated in image processor during the noise reduction process by referencing the status register (step S28). The error generation determination process of step S28 is described in detail below. When the value of the status register of the image processor 15 indicates a noise reduction process standby condition in the process of step S28 despite the noise reduction process execution instruction in step S25, the CPU 12 determines that the noise reduction process has not started and an error has been generated in the image processor 15. Furthermore, even when a currently executing noise reduction process status has been set, an error generation in the image process or 15 is determined when the noise reduction process has not ended after a predetermined time has elapsed after the start of the noise reduction process, that is, when the a currently executing noise reduction process status has been set. When an error is detected (step S28: YES), the CPU 12 sets an error code associated beforehand to the error (step S29), and the process moves to step S67. Thus, it is possible to determine whether or not the median filter process circuit in the image processor 15 is functioning normally by determining whether or not the median filter process circuit is executing the noise reduction process normally. That is, when an abnormality is detected, it is possible to detect that the median filter process circuit is the location of the abnormality even within the image processor 15.

When the noise reduction process ends, the image processor 15 sends the treated test background image data to the CPU 12 (step S30). When an error is not detected in step S28 (step S28: NO), the CPU 12 receives the test background image data from the image processor 15 (step S31), and generates a background correction image described in the normal running operation (step S32). The CPU 12 stores the data of the generated background correction image in the background correction data memory 18 (step S33).

The flash memory card reader 22 reads test images 25 stored on the flash memory card 22a (step S34), and the CPU 12 receives the data. The CPU 12 determines whether or not an error has been generated when the data are read by the flash memory card reader 22 (step S35). The process of step S35 is identical to the process of step S22, and, therefore, further description is omitted. When an error is detected (step S35: YES), the CPU 12 sets an error code associated beforehand to the error (step S36), and the process moves to step S67.

When an error is not detected in step S35 (step S35: NO), the CPU 12 stores the data of test image 25 of the image processor 15 in the frame buffer 16 (step S37). Then, the CPU 12 instructs the image processor 15 to execute the noise reduction process (step S38). The image processor 15 receives the instruction to execute the noise reduction process (step S39), and executes the noise reduction process on test images 25 stored in the frame buffer 16 (step S40). The CPU 12 determines whether or not an error has been generated in the image processor 15 during the noise reduction process (step S41). The process of step S41 is identical to the process of step S28, and, therefore, further description is omitted. When an error is detected (step S41: YES), the CPU 12 sets an error code associated beforehand to the error (step S42), and the process moves to step S67.

When the noise reduction process ends, the image processor 15 executes the background correction process described in the normal running operation using the processed test images and the background correction images stored in the background correction data memory 18 (step S43). Furthermore, the image processor 15 executes the contour enhancement process described in the normal running operation after the background correction process has ended (step S44), and sets the binarization threshold level described in the normal running operation after the contour enhancement process ends (step S45). When an error is not detected in step S41 (step S41: NO), the CPU 12 determines whether or not an error has been generated by the image processor 15 in the contour enhancement process S44 and binarization threshold setting process S45 (step S46). The image processor 15 sets the status information indicating the currently executing/standby contour enhancement process or binarization threshold setting process to an internal status register (not shown in the drawing), and in step S46 the CPU 12 determines whether or not an error has been generated in the image processor 15 during the contour enhancement process and binarization threshold setting process by referencing the status register. The principle of the error detection process of step S46 is identical to the principle of the error process of step S28, and, therefore, further description is omitted. When an error is detected (step S46: YES), the CPU 12 sets an error code associated beforehand to the error (step S47), and the process moves to step S67. In this way it is possible to determine whether or not the Laplacean filter process circuit in the image processor 15 is functioning normally by determining whether or not the contour enhancement process and binarization threshold setting process are executed normally by the Laplacean filter process circuit. That is, when an abnormality is detected, it is possible to detect that the Laplacean filter process circuit is the location of the abnormality even within the image processor 15.

When the contour enhancement process and binarization threshold setting process end, the image processor 15 executes the binarization process on the Laplacean processed image (step S48) as described in the normal running operation; when the execution of the binarization process ends, the image processor 15 acquires prime codes and multiple point information (step S49) as described in the normal running operation; and when the prime code and multiple point information acquisition processes end, the image processor 15 generates vertex data (step S50) as described in the normal running operation. When an error is not detected in step S46 (step S46: NO), the CPU 12 determines whether or not an error has been generated by the image processor 15 in the binarization process S48, prime code and multiple point information acquisition process S49, and vertex data generation process S50 (step S51). The image processor 15 sets the status information indicating the currently executing/standby binarization process, prime code and multiple point acquisition process, and vertex data generation process; and in step S51, the CPU 12 determines whether or not an error has been generated by the image processor 15 during the execution of the binarization process, prime code and multiple point acquisition process, and vertex data generation process by referencing the status register. The principle of the error detection process of step S51 is identical to the principle of the error process of step S28, and, therefore, further description is omitted. When an error is detected (step S51: YES), the CPU 12 sets an error code associated beforehand to the error (step S52), and the process moves to step S67. In this way it is possible to determine whether or not the binarization process circuit in the image processor 15 is functioning normally by determining whether or not the binarization process, prime code and multiple point information acquisition process, and vertex data generation process are executed normally by the binarization process circuit. That is, when an abnormality is detected, it is possible to detect that the binarization process circuit is the location of the abnormality even within the image processor 15.

The image processor 15 executes the edge tracing process as described in the normal running operation (step S53) when the binarization process, prime code and multiple point information acquisition process, and vertex data generation process end. When an error is not detected in step S51 (step S51: NO), the CPU 12 determines whether or not an error has been generated by the image processor 15 in the edge tracing process S53 (step S54). At this time the image processor 15 sets status information indicating the currently executing/standby edge tracing process to an internal status register (not shown in the drawing), and in step S54 the CPU 12 determines whether or not an error has been generated in image processor during the execution of the edge tracing process by referencing the status register. The principle of the error detection process of step S54 is identical to the principle of the error process of step S28, and, therefore, further description is omitted. When an error is detected (step S54: YES), the CPU 12 sets an error code associated beforehand to the error (step S52), and the process moves to step S67. In this way it is possible to determine whether or not the edge tracing process circuit in the image processor 15 is functioning normally by determining whether or not the edge tracing process is executed normally by the edge tracing process circuit. That is, when an abnormality is detected, it is possible to detect that the edge tracing process circuit is the location of the abnormality even within the image processor 15.

The image processor 15 executes the particle overlap check process (step S56) as described in the normal running operation when the edge tracing process ends. When an error is not detected in step S54 (step S54: NO), the CPU 12 determines whether or not an error has been generated by the image processor 15 in the overlap check process S56 (step S57). At this time the image processor 15 sets status information indicating the currently executing/standby overlap check process to an internal status register (not shown in the drawing), and in step S57 the CPU 12 determines whether or not an error has been generated in image processor 15 during the execution of the overlap check process by referencing the status register. The principle of the error detection process of step S57 is identical to the principle of the error process of step S28, and, therefore, further description is omitted. When an error is detected (step S57: YES), the CPU 12 sets an error code associated beforehand to the error (step S58), and the process moves to step S67. In this way it is possible to determine whether or not the overlap check process circuit in the image processor 15 is functioning normally by determining whether or not the overlap check process is executed normally by the overlap check process circuit. That is, when an abnormality is detected, it is possible to detect that the overlap check process circuit is the location of the abnormality even within the image processor 15.

The image processor 15 executes the image processing result data generating process (step S59) as described in the normal running operation when the overlap check process ends. When an error is not detected in step S57 (step S57: NO), the CPU 12 determines whether or not an error has been generated by the image processor 15 in the result data generation process S59 (step S60). At this time the image processor 15 sets status information indicating the currently executing/standby result data generation process to an internal status register (not shown in the drawing), and in step S60 the CPU 12 determines whether or not an error has been generated in image processor 15 during the execution of the result data generation process by referencing the status register. The principle of the error detection process of step S60 is identical to the principle of the error process of step S28, and, therefore, further description is omitted. When an error is detected (step S60: YES), the CPU 12 sets an error code associated beforehand to the error (step S61), and the process moves to step S67. In this way it is possible to determine whether or not the result data generation circuit in the image processor 15 is functioning normally by determining whether or not the result data generation process is executed normally by the result data generation circuit. That is, when an abnormality is detected, it is possible to detect that the result data generation circuit is the location of the abnormality even within the image processor 15.

When an error is not detected in step S60 (step S60: NO), the CPU 12 reads the image processing result data from the result data memory 21 (step S62), and reads the test result data 27 recorded on the flash memory card 22a (step S63). Then, by comparing the image processing result data and the test result data 27 (step S64), a determination is made as to whether or not an error has been generated in the image processor 15 by the result of the comparison (step S65). When image process has been accomplished normally, the image processing result data and test result data will match; whereas when the data do not match, an error is generated in the image processor 15. Accordingly, when an error is detected in step S65 (step S65: YES), the CPU 12 sets an error code associated beforehand to the error (step S66), and the process moves to step S67. Furthermore, the CPU 12 moves the process to step S67 even when an error is not detected in step S65.

When an error is not detected in the aforesaid process, the CPU 12 generates test result data indicating that the image processor 15 is normal, or when an error is detected, generates test result data including an error code of the detected error, and then stores the data in the main memory 14 (step S67). Then the CPU 12 awaits request data for the test result data from the CPU printed circuit board 5 (step S68). When request data are receives from the CPU circuit board 5 (step S68: YES), the test result data are transmitted to the CPU circuit board 5 (step S69), and the process ends.

Thereafter, communication starts between the CPU circuit board 5 and the data processing unit 3, and when the transmission request for test result data is received from the data processing unit 3, the test result data are transmitted to the image processing unit 3. In the data processing unit 3, the test result representing the test result data is displayed on the screen of a display device. For example, when an error code is included in the test result data, the data processing unit 3 displays the error code on the test result screen. In this way a user or maintenance personnel for the particle image analyzer 1 can confirm the error code, and specify the location generating the error and the type of error generated in the image processing circuit board 4.

Furthermore, the aforesaid structure provides that the functions required for normal running operation of the image processor 15 are guaranteed insofar as an abnormality is not detected in the self testing operation since, in the self testing operation, the image processes required for normal running operation are actually executed, and a determination made as to whether or not the image processes are executed normally.

Furthermore, a SCAN circuit, BIST (built in self test) circuit and the like can be provided in the image processor 15, so as to combine a self testing function of the image processor 15 by such circuits, the self testing function of the image processor 15 of the present embodiment, and other test functions, and thereby improve the accuracy of the self test. The image processing circuit testing method of the present embodiment does not require that a special testing circuit is built into the image processor 15 as described above, thereby reducing the number of development processes and number of design processes.

In the image processing circuit testing method of the present embodiment, it is possible to detect abnormalities that are not detectable by other testing methods.

In the particle image analyzer 1 of the present embodiment, the image processor 15 is divided into a plurality of function blocks, including a median filter process circuit, Laplacean filter process circuit, binarization process circuit, edge tracing process circuit, overlap check circuit, result data generation circuit and the like. When a plurality of processes must be executed in the image processing circuit, the image processing circuit may be divided into narrow function blocks to increase development efficiency and maintenance efficiency and debugging and evaluation of these function blocks can be often performed as in the case of the image processor 15 of the present embodiment. Therefore, the functions (programs) used for development can be realized as is for debugging, or appropriated for the testing functions (programs) of the present embodiment. Accordingly, when the image processing circuit is divided into a plurality of function blocks and used for development, debugging and evaluations, development is efficiency and design efficiency is greatly improved.

In the embodiment described above, the test result data 27 includes partial images 29 and feature information 31, and the comparison process of step S64 is structured so as to compare test result data 27 and the partial images, position information, area values, linear count number, slope count number, and corner count number generated by the image process of the image processor 15, however, the present invention is not limited to this arrangement inasmuch as, for example, only the test partial images might be provided beforehand, and these test partial images might be compared with partial images generated in the image processes.

Although the present embodiment has been described in terms of testing an integrated circuit image processor 15, the present invention is not limited to this arrangement inasmuch as, for example, an entire image processing circuit including an IC image processor and other digital circuits may be tested, or other structures of image processing circuits may be tested insofar as the object of test are circuits specific to image process.

In the present embodiment, test image 25, test background image 26, and test result data 27 are stored beforehand on the flash memory card 22a, and the programs and data are read by the flash memory card reader 22, however, the present invention is not limited to this arrangement inasmuch as, for example, the test image 25, test background image 26, and test result data 27 may be stored beforehand on a recording medium such as a CD, DVD or the like, and the programs and data are read by other media reading devices such as a CD drive, DVD drive or the like capable of reading the medium.

In the present embodiment, a computer program related to the self testing function of the image processor 15 is executed by the CPU 12 provided in the image processing printed circuit board 4, and when the CPU 12 has executed the computer program, a processing request is issued to the image processor 15 and image processing is executed; however, the present invention is not limited to this arrangement inasmuch as, for example, a CPU may be built into the CPU printed circuit board 5, CPU may be provided in the data processing unit 3 or the like, and the self testing function of the image processor 15 may be executed by the CPU external to the image processing printed circuit board 4, such that when a computer program is executed by such CPU, a processing request is issued from the CPU to the image processor 15 and image processing is executed.

Furthermore, in the present embodiment, the self testing computer program 30 is independent of the other control programs of the image processing printed circuit board 4, and the self testing computer program 30 is stored on the flash memory card 22a, however, the present invention is not limited to this arrangement inasmuch as self testing computer program may be integrated within the control programs of the image processing printed circuit board 4 as a routine program, and this control program may be stored on the flash memory card 22a.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A method for analyzing a particle contained in a liquid comprising steps of:
controlling, by a processor, an image processing circuit so as to execute a predetermined image process on a test image which contains a test particle image;
comparing, by the processor an image processing result of the test image by the image processing circuit with a predetermined test image processing result;
determining, by the processor, whether or not the image processing circuit is functioning normally based on the comparing result;
imaging a particle contained in a liquid passing through a flow cell by an imaging part, when it has been determined that the image processing circuit is functioning normally;
obtaining, by the processor, feature information representing feature of a particle image contained in an image obtained by the imaging part, by controlling the image processing circuit so as to execute the predetermined image process on the image obtained by the imaging part; and
displaying, on a display, information indicating that the image processing circuit is not functioning normally, when it has been determined that the image processing circuit is not functioning normally.

2. The method of claim 1, wherein
the image processing circuit extracts a partial image containing one particle image from an image containing a particle image by executing the predetermined image process on the image;
the step of controlling the image processing circuit comprises a step of extracting a partial image containing one particle image from the test image using the image processing circuit; and
the step of comparing comprises a step of comparing the image processing result containing the partial image of the test image extracted by the image processing circuit, with the predetermined test image processing result containing a test partial image equivalent to a partial image extracted from the test image by the image processing circuit during normal operation.

3. A particle analyzer for analyzing a particle contained in a liquid comprising:
a flow cell for passing a liquid containing a particle;
an imaging part for imaging the particle contained in the liquid passing through the flow cell;
an image processing circuit for executing a predetermined image process on a an image containing a particle image;
a controller for controlling the image processing circuit so as to execute the predetermined image process on a test image containing a test particle image, comparing an image processing result of the test image by the image processing circuit with a predetermined test image processing result, and determining whether or not the image processing circuit is functioning normally based on the comparing result; and a display device;

wherein the controller controls the imaging part so as to image the particle contained in the liquid passing through the flow cell, when the controller has determined that the image processing circuit is functioning normally, and obtains feature information representing feature of a particle image contained in an image obtained by the imaging part by controlling the image processing circuit so as to execute the predetermined image process on the image obtained by the imaging part; and wherein the display device displays information indicating that the image processing circuit is not functioning normally when the controller has determined that the image processing circuit is not functioning normally.

4. The particle image analyzer of claim 3 further comprising a recording medium for storing the predetermined test image processing results beforehand.

5. The particle image analyzer of claim 3, wherein
the image processing circuit extracts a partial image containing one particle image by executing a predetermined image process on the image;
the predetermined test image processing result includes a predetermined test partial image; and
the controller compares the predetermined test image processing result with the image processing result which includes a partial image extracted from the test image by the image processing circuit.

6. The particle image analyzer of claim 3, wherein the image processing circuit comprises a noise reduction part for executing a noise reduction process on the image containing the particle image.

7. The particle image analyzer of claim 6, wherein the controller determines whether or not an error has been generated in the noise reduction process by the noise reduction part.

8. The particle image analyzer of claim 7, wherein the controller determines whether or not the noise reduction process by the noise reduction part has started; and determines whether or not the noise determination process by the noise determination part has ended.

9. The particle image analyzer of claim 3, wherein the image processing circuit comprises a background correction part for correcting a background of the image containing the particle image.

10. The particle image analyzer of claim 3, wherein the image processing circuit comprises a contour enhancing part for executing a contour enhancement process on the image containing the particle image.

11. The particle image analyzer of claim 10, the controller determines whether or not an error has been generated in the contour enhancement process by the contour enhancement part.

12. The particle image analyzer of claim 11, wherein the controller determines whether or not the contour enhancement process by the contour enhancement part has started; and determines whether or not the contour enhancement process by the contour enhancement part has ended.

13. The particle image analyzer of claim 3, wherein the image processing circuit comprises a binarization part for executing a binarizing process on the image containing the particle image.

14. The particle image analyzer of claim 13, wherein the controller determines whether or not an error has been generated in the binarizing process by the binarization part.

15. The particle image analyzer of claim 14, wherein the controller determines whether or not the binarizing process by the binarization part has started and determines whether or not the binarizing process by the binarization part has ended.

16. The particle image analyzer of claim 14, wherein the image processing circuit comprises an edge extraction part for executing an edge extraction process on the binarized image.

17. The particle image analyzer of claim 16, the controller determines whether or not an error has been generated in the edge extraction process by the edge extraction part.

18. The particle image analyzer of claim 17, wherein the controller determines whether or not the edge extraction process by the edge extraction part has started; and determines whether or not the edge extraction process by the edge extraction part has ended.

19. The particle image analyzer of claim 3, wherein
the image processing circuit comprises a feature information acquisition part for acquiring feature information representing the features of the particle image;
the predetermined test image processing result includes test predetermined feature information; and
the controller compares the predetermined test image processing result with the image processing result which includes feature information generated when the image process is executed on the test image by the image processing circuit.

20. The particle image analyzer of claim 19, wherein the feature information acquisition part comprises;
a position information acquisition part for acquiring position information representing the position at which a particle is present in the particle image containing the particle image;
an edge information acquisition part for acquiring information relating to linear components, slope components, and corner components of an edge of the particle image; and
an area value acquisition part for acquiring a surface area value of the particle image;
and wherein the test feature information includes information respectively equivalent to position information, information relating to linear components, slope components, and corner components of the edge of the particle image, and information of a surface area value of the particle image obtained when image process is executed on the test image by the image processing circuit during normal operation.

21. The particle image analyzer of claim 4, wherein the controller determines whether or not an error has been generated when information is read from the storage medium.

22. A computer readable storage medium for storing a computer program for analyzing, on a computer, a particle contained liquid wherein
the computer program comprises software instructions for enabling the computer to perform predetermined operations, comprising:
controlling an image processing circuit so as to execute a predetermined image process on a test image containing a test particle image;
reading, from a memory, a predetermined test image processing result recorded beforehand on the memory;
comparing the test processing result read from the memory with an image processing result obtained by executing the predetermined image process on the test image;

determining whether or not the image processing circuit is functioning normally based on the comparing result;

controlling an imaging part so as to image a particle contained in a liquid passing through a flow cell, when it has been determined that the image processing circuit is functioning normally;

obtaining feature information representing feature of a particle image contained in an image obtained by the imaging part, by controlling the image processing circuit so as to execute the predetermined image process on the image obtained by the imaging part; and controlling a display so as to display information indicating that the image processing circuit is not functioning normally, when it has been determined that the image processing circuit is not functioning normally.

* * * * *